US012616959B2

(12) United States Patent
Katryniok et al.

(10) Patent No.: US 12,616,959 B2
(45) Date of Patent: May 5, 2026

(54) PRODUCTION OF ALLYL ALCOHOL FROM GLYCEROL USING A REUSABLE CATALYST MADE FROM RHENIUM

(71) Applicants: CENTRE NATIONAL DE LA RECHERCHE SCIENTIFIQUE, Paris (FR); CENTRALE LILLE INSTITUT, Villeneuve d'Ascq (FR); UNIVERSITÉ DE LILLE, Lille (FR)

(72) Inventors: Benjamin Katryniok, La Bassee (FR); Karen Silva, Lille (FR); Marcia Araque, Lille (FR)

(73) Assignees: CENTRE NATIONAL DE LA RECHERCHE SCIENTIFQUE, Paris (FR); CENTRALE LILLE INSTITUT, Villeneuve d'Ascq (FR); UNIVERSITÉ DE LILLE, Lille (FR)

( * ) Notice: Subject to any disclaimer, the term of this patent is extended or adjusted under 35 U.S.C. 154(b) by 544 days.

(21) Appl. No.: 17/907,359

(22) PCT Filed: Mar. 24, 2021

(86) PCT No.: PCT/EP2021/057525
§ 371 (c)(1),
(2) Date: Sep. 26, 2022

(87) PCT Pub. No.: WO2021/191249
PCT Pub. Date: Sep. 30, 2021

(65) Prior Publication Data
US 2023/0112595 A1 Apr. 13, 2023

(30) Foreign Application Priority Data

Mar. 27, 2020 (FR) ...................................... 2003019

(51) Int. Cl.
| | |
|---|---|
| *B01J 23/36* | (2006.01) |
| *B01J 23/10* | (2006.01) |
| *B01J 35/61* | (2024.01) |
| *B01J 37/02* | (2006.01) |
| *B01J 37/08* | (2006.01) |
| *C07C 29/60* | (2006.01) |

(52) U.S. Cl.
CPC ............... *B01J 23/36* (2013.01); *B01J 23/10* (2013.01); *B01J 35/615* (2024.01); *B01J 37/0201* (2013.01); *B01J 37/082* (2013.01); *C07C 29/60* (2013.01)

(58) Field of Classification Search
CPC . B01J 23/36; B01J 35/615; B01J 23/10; B01J 37/0201; B01J 37/082; C07C 29/60
See application file for complete search history.

(56) References Cited

U.S. PATENT DOCUMENTS 10,500,567 B2 * 12/2019 Kon et al. ............... C07C 29/60

FOREIGN PATENT DOCUMENTS

EP 3 124 462 A1 2/2017

OTHER PUBLICATIONS

ACS Catal. 2016, 6, 677-680 (Sandbrink et al., with Supporting Information) (Year: 2016).*
Sandbrink et al: "ReO x /TiO 2 : A Recyclable Solid Catalyst for Deoxydehydration", ACS Catalysis, vol. 6, No. 2, p. 677-680, Feb. 5, 2016.
Tazawa et al: "Deoxydehydration with Molecular Hydrogen over Ceria-Supported Rhenium Catalyst with Gold Promoter", ACS Catalysts, vol. 6, No. 10, p. 6393-6397, Oct. 7, 2016.

* cited by examiner

*Primary Examiner* — Amy C Bonaparte
*Assistant Examiner* — Derek Rhoades
(74) *Attorney, Agent, or Firm* — WCF IP

(57) ABSTRACT

The present invention relates to the use of a catalyst made of rhenium oxide supported by cerium oxide, with formula $ReO_x/CeO_2$ (I), for catalyzing the deoxydehydration of glycerol to allyl alcohol, the reaction being carried out under heterogeneous conditions in the presence of at least one aliphatic alcohol; and to a method for producing allyl alcohol from glycerol in the presence of the catalyst.

14 Claims, No Drawings

PRODUCTION OF ALLYL ALCOHOL FROM GLYCEROL USING A REUSABLE CATALYST MADE FROM RHENIUM

The present invention relates to the use of supported heterogeneous catalysts containing rhenium for the production of allyl alcohol from glycerol and to a method for producing allyl alcohol from glycerol in the presence of such heterogeneous catalysts.

Allyl alcohol is known as a valuable material in the chemical industry. Allyl alcohol can be used as such, but also as a raw material for producing a variety of high tonnage chemicals such as acrolein, acrylic acid or acrylonitrile. Allyl alcohol is also used as an allylating agent in modern organic chemistry (Sundararaju et al, Chem. Soc. Rev., 2012, 41, 4467-4483).

At present, allyl alcohol is obtained by selective hydrogenation of acrolein which is itself most conventionally resulting from a process of selective oxidation of propylene. Glycerol is one of the most important renewable platform molecules, because same is a co-product of the transesterification process for biodiesel production (about 100 kg of glycerol are produced per ton of biodiesel). The recent expansion of the biodiesel market has led to an overabundance of glycerol, which makes same very attractive as a substrate for the synthesis of more valuable chemicals.

Efficient processes of converting glycerol into useful chemicals are intensively studied around the world therefore. In particular, the processes of converting allyl alcohol into acrolein and/or acrylic acid are well established, but the efficient and sustainable generation of allyl alcohol from biosourced glycerol, thus coming from a renewable resource, has never been carried out in practice. In addition, such reactions generally require catalysts.

Different processes of synthesizing allyl alcohol from glycerol using rhenium-containing catalysts have been reported. E.g. Canale et al. (Catal. Sci. Technol., 2014, 4, 3697-3704) report that the deoxydehydration of glycerol into allyl alcohol is catalyzed by rhenium derivatives, either in pure glycerol or in the presence of solvents (in particular alcohols), under an air atmosphere or under hydrogen sparging. In particular, the reaction carried out at 140° C. in air, using 1-hexanol or 2,4-dimethyl-3-pentanol as solvents, led to allyl alcohol with yields of 28% and 61%, respectively, using methyltrioxorhenium (MTO) as catalyst, and to allyl alcohol with yields of 20% and 64%, respectively, using ReO$_3$ as catalyst. However, said catalysts exhibit significant deactivation after a single test. Moreover, MTO is not easy to recover after use because same is dissolved in the liquid phase (homogeneous catalyst).

Some attempts have also been made to use supported heterogeneous catalysts for carrying out the conversion of glycerol into allyl alcohol. In particular, there are numerous reports on the synthesis of allyl alcohol from glycerol using solid iron oxide catalysts supported in the gas phase (see e.g. Sanchez et al., Appl. Catal. B: Environmental 2014, 152-153, 117-128). However, according to such processes, the allyl alcohol yields are limited to 32% (Wang et al., Chem. J. Chin. Univ. 2013, 34, 650-655).

Application EP3124462 also describes a process of direct deoxydehydration of glycerol into allyl alcohol, using a heterogeneous catalyst containing alumina-supported rhenium oxide with the formula ReO$_3$/Al$_2$O$_3$, in the presence of at least one aliphatic alcohol.

However, there is still a need for an improved process for the production of allyl alcohol from glycerol, with very good productivity.

The present invention addresses said problem: the process according to the invention aims to produce allyl alcohol from glycerol, with a high yield and a very good productivity. Such process uses a heterogeneous catalyst rhenium on a cerium oxide support with the formula ReO$_x$/CeO$_2$.

A first subject matter of the present invention is thus the use of a catalyst containing rhenium supported by cerium oxide with the formula ReO$_x$/CeO$_2$ (I), for catalyzing the deoxydehydration of glycerol into allyl alcohol, said reaction being carried out under heterogeneous conditions and in the presence of at least one aliphatic alcohol.

The catalysts with the above formula (I) can be used for carrying out the deoxydehydration of glycerol into allyl alcohol on a practical scale with a yield of up to about 90%, i.e. say much higher than with the supported iron oxide catalysts of the prior art. Moreover, such catalysts can be used for carrying out such reaction with a much better productivity than the catalysts with the formula ReO$_3$/Al$_2$O$_3$. Finally, the catalysts with the formula (I) can be reused and be easily recovered from the reaction mixture.

Among the catalysts with the formula (I) above, the catalyst in which the amount of ReO$_x$ varies from 2% to 20% by weight with respect to the total mass of catalyst with the formula (I) are preferred, more particularly, the catalysts in which the amount of ReO$_x$ varies from 3% to 15% by weight, and preferentially from 4% to 12% by weight.

As an example, the catalysts with the above formula (I) can in particular be prepared by an incipient wetness impregnation of cerium oxide (CeO$_2$) with an aqueous solution of perrhenic acid (HReO$_4$). After impregnation, the resulting catalyst with the formula (I) is preferentially dried at a temperature ranging from about 100° C. to 150° C. for several hours, and then calcined.

Another subject matter of the present invention is a process of production of allyl alcohol from glycerol in the presence of a catalyst, said process comprising only one glycerol dehydration step, said reaction being carried out under heterogeneous conditions, in the presence of i) a catalyst containing rhenium oxide supported on cerium oxide, with the formula ReO$_x$/CeO$_2$ (I) and (ii) at least one aliphatic alcohol.

The process according to the invention comprises one step, i.e. the process can be used for obtaining allyl alcohol from glycerol in a single step.

The process according to the invention can be used for producing allyl alcohol without using raw materials coming from fossil resources. The process is simple to carry out (a single step) and is very selective. The result of same is allyl alcohol, with yields of up to about 90%.

According to a preferred embodiment of the process according to the invention, the catalyst with the formula (I) is chosen from catalysts in which the amount of ReO$_x$ ranges from about 2 to 20% by weight with respect to the total mass of catalyst with the formula (I), and more particularly, catalysts in which the amount of ReO$_x$ varies from 3% to 15% by weight, and preferentially from 4% to 12% by weight.

According to a preferred embodiment of the invention, the specific surface area of the cerium oxide used to support ReO$_x$ ranges from about 100 m$^2$/g to 300 m$^2$/g and even more preferentially from 150 m$^2$/g to 250 m$^2$/g (BET method).

Aliphatic alcohol is used as a solvent. Aliphatic alcohol further acts as a reducing sacrificial agent during the conversion of glycerol into allyl alcohol.

According to a preferred embodiment of the present invention, the aliphatic alcohol is a monohydroxylated alcohol having from 6 to 10 carbon atoms, preferentially from 6 to 8 carbon atoms.

Among the monohydroxylated alcohols having from 6 to 10 carbon atoms, preferentially from 6 to 8 carbon atoms, secondary alcohols are preferred.

Among such secondary alcohols, of 2-hexanol and 3-octanol can be cited.

According to a particular and preferred embodiment of the present invention, the aliphatic alcohol is 2-hexanol.

The deoxydehydration reaction is preferentially carried out at a temperature greater than or equal to about 140° C. and more preferentially at a temperature ranging from about 140° C. to 150° C. A temperature of about 145° C. is even more particularly preferred according to the invention.

According to a preferred embodiment of the process according to the invention, the deoxydehydration reaction is carried out using glycerol with a purity of at least 80%, preferentially of at least 85%, preferentially of at least 90%, preferentially of at least 95%, preferentially of at least 99%. More preferentially, the deoxydehydration reaction is carried out using glycerol with a purity of at least 95%, preferentially of at least 99%.

As shown in the Example 19 and in Table 5, the studies carried out by the inventors have shown that the use of glycerol having a purity of less than 95%, i.e. containing more than 5% by weight of impurities, in particular more than 5% by weight of water, with respect to the total weight of glycerol, adversely affects the allyl alcohol yield.

After reaction, the separation of the co-products and by-products of the reaction can be carried out by any appropriate technique known to a person skilled in the art, e.g. by distillation.

The catalyst can easily be easily recovered, e.g. by filtration and then drying. Before a new use, and even if same is not mandatory, the catalyst can be calcined.

Preferentially, as indicated above, the catalyst containing rhenium oxide supported on cerium oxide with the formula $ReO_x/CeO_2$ (I) according to the invention is prepared by the incipient wetness impregnation method. The above situation is illustrated in particular in the Example 1. According to such a method, typically, the volume of impregnation solution (i.e. aqueous solution of perrhenic acid ($HReO_4$)) used is equal to the pore volume of the support ($CeO_2$).

The present invention is illustrated, but not limited to, by the following examples.

EXAMPLE 1

Preparation of a Cerium-Supported Rhenium Oxide Catalyst ($ReO_x/CeO_2$) According to the Invention Rhenium catalysts supported on cerium (HAS-5, marketed by SOLVAY) were prepared by the incipient wetness impregnation method. The BET surface area of HAS-5 is 246 m$^2$/g. For the preparation of 10% by weight of $ReO_x/CeO_2$ (i.e. comprising 10% by weight of $ReO_x$ with respect to the total weight of catalyst), first, $CeO_2$ (HAS-5, 2 g) was washed with distilled water using vacuum filtration, then was dried and calcined in static air at 110° C. (12 h) and 500° C. (3 h), respectively. After that, same was added to a dilute aqueous solution of $HReO_4$ solution, which was obtained by mixing 400 mg of the aqueous solution containing 75% by weight of $HReO_4$ (Aldrich) with water (0.75 ml). The impregnated catalyst was dried at 110° C. for 12 h and calcined in static air at 500° C. for 3 hours using a heating rate of 5° C./min.

EXAMPLE 2

Reaction of Glycerol for Obtaining Allyl Alcohol Using 10% by Weight of $ReO_x/CeO_2$ Catalyst According to the Invention (1st Use of the Catalyst)

A pressure-resistant glass tube equipped with a magnetic stirring bar was filled with glycerol (92 mg, 1 mmol, purity in water>99%), 10% by weight of $ReO_x/CeO_2$ (100 mg; obtained in the Example 1) and 2-hexanol (3.3 ml). The container was hermetically closed by a screw cap and the mixture was stirred (1300 rpm) in an oil bath maintained at 175° C. for 2 h so that the reaction medium was maintained at a reaction temperature of 145° C. Although 2-hexanol has, at atmospheric pressure, a boiling point of 136° C., the preferred reaction temperature is above 136° C. After reaction, the solution was cooled to room temperature and then recovered; 1 ml was collected for analysis by gas chromatography. Benzene (9 mg, 0.115 mmol) was added to the solution, and the mixture was then well mixed in an ultrasonic bath for 10 min at 60° C. The conversion and selectivity were determined by GC analysis using benzene as the internal standard.

The results are shown in Table 1. The allyl alcohol yield was 54%, the glycerol conversion was 74% and the allyl alcohol selectivity was 73%.

Table 1. Results of the Reaction of Glycerol in Allyl Alcohol Using 10% by Weight of $ReO_x/CeO_2$ in 2-Hexanol [a]

TABLE 1

| Experiment | Catalyst | Yield (%) (d) | Conversion (%) (c) | Selectivity (%) (c) | Comment |
|---|---|---|---|---|---|
| 1 | 10%* by weight of $ReO_x/CeO_2$ | 54 | 74 | 73 | 1$^{st}$ use |
| 2 | 10%* by weight of $ReO_x/CeO_2$ | 54 | 77 | 70 | 2$^{nd}$ use |
| 3 | 10%* by weight of $ReO_x/CeO_2$ | 58 | 80 | 74 | 3$^{rd}$ use |

[a] Reaction conditions: glycerol (92 mg, 1 mmol), catalyst (100 mg) and 2-hexanol (3.3 ml), oil bath at 175° C., 1300 rpm, 2 h, unless otherwise indicated
(c) Selectivity and conversion determined by GC analysis
(d) Yield = Selectivity * Conversion/100
*Comprising 10% by weight of $ReO_x$ with respect to the total weight of catalyst.

EXAMPLE 3

Reaction of Glycerol for Obtaining Allyl Alcohol Using 10% by Weight of $ReO_x/CeO_2$ Catalyst According to the Invention (2$^{nd}$ Use of Catalyst) (Experiment 2)

The reaction was carried out as in the Example 2, but using the 10% by weight of $ReO_x/CeO_2$ from experiment 1 with a new quantity of glycerol. The 10% by weight of $ReO_x/CeO_2$ used was reused without prior washing, drying or calcination.

The allyl alcohol yield was 54%, the glycerol conversion was 77% and the allyl alcohol selectivity was 70%.

EXAMPLE 4

Reaction of Glycerol for Obtaining Allyl Alcohol
Using 10% by Weight of $ReO_x/CeO_2$ Catalyst
According to the Invention ($3^{rd}$ Use of Catalyst)
(Experiment 3)

The reaction was carried out as in the Example 3, but using the 10% by weight of $ReO_x/CeO_2$ from experiment 2 with a new quantity of glycerol. The 10% by weight of $ReO_x/CeO_2$ used was reused without prior washing, drying or calcination.

The allyl alcohol yield was 58%, the glycerol conversion was 80% and the allyl alcohol selectivity was 74%.

Results

The catalyst was easily reused for producing allyl alcohol with yields of 54% and 58% for a second and a third use, respectively (Table 1, experiments 1 to 3). No peak attributed to acrolein or acrylic acid was observed.

EXAMPLE 5

Reaction of Glycerol for Obtaining Allyl Alcohol
Using $CeO_2$ (HAS-5) (Comparative)

The reaction was carried out as in the Example 2, but using $CeO_2$ (HAS-5, 100 mg) and 2.5 h of reaction time.
The allyl alcohol yield was 0%, the glycerol conversion was 3% and the allyl alcohol selectivity was 0%.

EXAMPLE 6

Reaction of Glycerol for Obtaining Allyl Alcohol
Using 2.5% by Weight of $ReO_x/CeO_2$ Catalyst
According to the Invention (i.e. Comprising 2.5%
by Weight of $ReO_x$ with Respect to the Total
Weight of Catalyst)

The reaction was carried out as in the Example 2, but using 2.5% by weight of $ReO_x/CeO_2$ (100 mg) and 2.5 h of reaction time.
The conditions for preparing the catalyst were as in the Example 2, but using a dilute aqueous solution of $HReO_4$, which was obtained by mixing 93 mg of the aqueous solution containing 75% by weight of $HReO_4$ (Aldrich) with water (0.75 ml).
The allyl alcohol yield was 77%, the glycerol conversion was 91% and the allyl alcohol selectivity was 84%.

EXAMPLE 7

Reaction of Glycerol for Obtaining Allyl Alcohol
Using 5% by Weight of $ReO_x/CeO_2$ Catalyst
According to the Invention (i.e. Comprising 5% by
Weight of $ReO_x$ with Respect to the Total Weight
of Catalyst)

The reaction was carried out as in the Example 2, but using 5% by weight of $ReO_x/CeO_2$ (100 mg) and 2.5 h of reaction time.
The conditions for preparing the catalyst were as in the Example 2, but using a dilute aqueous solution of $HReO_4$, which was obtained by mixing 190 mg of the aqueous solution containing 75% by weight of $HReO_4$ (Aldrich) with water (0.75 ml).

The allyl alcohol yield was 84%, the glycerol conversion was >99% and the allyl alcohol selectivity was 84%.

EXAMPLE 8

Reaction of Glycerol for Obtaining Allyl Alcohol
Using 10% by Weight of $ReO_x/CeO_2$ Catalyst
According to the Invention (i.e. Comprising 10%
by Weight of $ReO_x$ with Respect to the Total
Weight of Catalyst) at an Increased Reaction Time The reaction was carried out as in the Example 2 using 10% by weight of $ReO_x/CeO_2$ (100 mg) but with 2.5 h of reaction time.
The preparation conditions for the catalyst were as in the Example 2. The allyl alcohol yield was 86%, the glycerol conversion was >99%, the allyl alcohol selectivity was 86%.

EXAMPLE 9

Reaction of Glycerol for Obtaining Allyl Alcohol
Using 15% by Weight of $ReO_x/CeO_2$ Catalyst
According to the Invention (i.e. Comprising 15%
by Weight of $ReO_x$ with Respect to the Total
Weight of Catalyst)

The reaction was carried out as in the Example 2, but using 15% by weight of $ReO_x/CeO_2$ (100 mg) and 2.5 h of reaction time.
The conditions for preparing the catalyst were as in the Example 2, but using a dilute aqueous solution of $HReO_4$, which was obtained by mixing 635 mg of the aqueous solution containing 75% by weight of $HReO_4$ (Aldrich) with water (0.75 ml).
The allyl alcohol yield was 81%, the glycerol conversion was >99%, the allyl alcohol selectivity was 81%.

Results

Experiments for optimizing the $ReO_x$ load were carried out (Table 2): the yield from the $CeO_2$ bare support was 0%, the yields increased with the increase in the $ReO_x$ load up to 10% by weight (77%, 84% and 86% for 2.5% by weight, 5% by weight and 10% by weight of $ReO_x$, respectively), but the yield slightly decreased for 15% by weight of $ReO_x/CeO_2$ (yield of 81%).

Table 2. Screening of the Rhenium Load on the Catalyst According to the Invention $ReO_x/CeO_2$ [a]

TABLE 2

| Example | Catalyst | Yield (%) (c) | Conversion (%) (b) | Selectivity (%) (b) |
|---------|----------|---------------|--------------------|--------------------|
| 5 | $CeO_2$ (comparative) | 0 | 3 | 0 |
| 6 | 2.5% by weight* of $ReO_x/CeO_2$ | 77 | 91 | 84 |
| 7 | 5% by weight* of $ReO_x/CeO_2$ | 84 | >99 | 84 |
| 8 | 10% by weight* of $ReO_x/CeO_2$ | 86 | >99 | 86 |

TABLE 2-continued

| Example | Catalyst | Yield (%) (c) | Conversion (%) (b) | Selectivity (%) (b) |
|---------|----------|---------------|--------------------|--------------------|
| 9 | 15% by weight* of $ReO_x/CeO_2$ | 81 | >99 | 81 |

[a] Reaction conditions: glycerol (92 mg, 1 mmol), catalyst (100 mg) and 2-hexanol (3.3 ml), oil bath at 175° C., 1300 rpm, 2.5 h, unless otherwise indicated
(b) Selectivity for allyl alcohol and glycerol conversion determined by GC analysis
(c) Yield = Selectivity * Conversion/100
*by weight of $ReO_x$ with respect to the total weight of catalyst.

EXAMPLE 10

Reaction of Glycerol for Obtaining Allyl Alcohol Using 3-Octanol

The reaction was carried out as in the Example 2, but using 3-octanol (3.3 ml) and 2.5 h of reaction time.

The allyl alcohol yield was 80%, the glycerol conversion was >99% and the allyl alcohol selectivity was 80%.

EXAMPLE 11

Reaction of Glycerol for Obtaining Allyl Alcohol Using 2-Pentanol

The reaction was carried out as in the Example 2, but using 2-pentanol (3.3 ml) and 2.5 h reaction time.

The allyl alcohol yield was 65%, the glycerol conversion was 82% and the allyl alcohol selectivity was 79%.

EXAMPLE 12

Reaction of Glycerol for Obtaining Allyl Alcohol Using 1-Heptanol

The reaction was carried out as in the Example 2, but using 1-heptanol (3.3 ml) and 2.5 h of reaction time.

The allyl alcohol yield was 22%, the glycerol conversion was 45% and the allyl alcohol selectivity was 48%.

EXAMPLE 13

Reaction of Glycerol for Obtaining Allyl Alcohol Using 2-Butanol

The reaction was carried out as in the Example 2, but using 2-butanol (3.3 ml) and 2.5 h of reaction time.

The allyl alcohol yield was 24%, the glycerol conversion was 37% and the allyl alcohol selectivity was 65%.

EXAMPLE 14

Reaction of Glycerol for Obtaining Allyl Alcohol Using Cyclohexanol

The reaction was carried out as in the Example 2, but using cyclohexanol (3.3 ml) and 2.5 h of reaction time.

The allyl alcohol yield was 21%, the glycerol conversion was 35% and the allyl alcohol selectivity (yield/conversion) was 59%.

Results

Various alcohols were tested with the catalyst containing 10% by weight of $ReO_x/CeO_2$ (Table 3). Secondary alcohols showed higher yields than primary alcohols (Table 3, Examples 8, 10-13). The aliphatic alcohol having longer chains also showed good reactivity leading to obtaining allyl alcohol with a yield of 80% (Table 3, Example 10). Short-chain aliphatic alcohols are good candidates if one is concerned about the cost, but the reactivity is lower than in the case of 2-hexanol (Table 3, Example 13, yield 24% in the case of 2-butanol). The cyclic alcohol showed a moderate yield (Table 3, Example 14).

Table 3. Screening of Alcohols with 10% by Weight of $ReO_x/CeO_2$ Catalyst According to the Invention (i.e. Comprising 10% by Weight of $ReO_x$ with Respect to the Total Weight of Catalyst) [a]

TABLE 3

| Example | Alcohol | Yield (%) (c) | Conversion (%) (b) | Selectivity (%) (b) |
|---------|---------|---------------|--------------------|--------------------|
| 8 | 2-hexanol | 86 | >99 | 86 |
| 10 | 3-octanol | 80 | >99 | 80 |
| 11 | 2-pentanol | 65 | 82 | 79 |
| 12 | 1-heptanol | 22 | 45 | 48 |
| 13 | 2-butanol | 24 | 37 | 65 |
| 14 | cyclohexanol | 21 | 35 | 59 |

[a] Reaction conditions: glycerol (92 mg, 1 mmol), 10% by weight of $ReO_x/CeO_2$ (100 mg) and alcohol (3.3 ml), oil bath at 175° C., 1300 rpm, 2.5 h, unless otherwise indicated
(b) Selectivity for allyl alcohol and glycerol conversion determined by GC analysis
(c) Yield = Selectivity * Conversion/100.

EXAMPLE 15

Reaction of Glycerol for Obtaining Allyl Alcohol in an Oil Bath with a Temperature of 165° C.

The reaction was carried out as in the Example 2, but using 165° C. as the oil bath temperature and 2.5 h reaction time.

The allyl alcohol yield was 62%, the glycerol conversion was 88% and the allyl alcohol selectivity was 71%.

EXAMPLE 16

Reaction of Glycerol for Obtaining Allyl Alcohol in an Oil Bath with a Temperature of 185° C.

The reaction was carried out as in the Example 2, but using 185° C. as the oil bath temperature and 2.5 h reaction time.

The allyl alcohol yield was 81%, the glycerol conversion was >99% and the allyl alcohol selectivity was 81%.

Results

Experiments for optimizing the reaction temperature were carried out with 10% by weight of $ReO_x/CeO_2$ catalyst according to the invention (Table 4). The yields increased with the increase in temperature up to 175° C. (oil bath) (yields 62% and 86% for 165° C. and 175° C. temperatures, respectively, of the oil bath), but the yield decreased slightly using a temperature of 185° C. (81% Yield).

Table 4. Screening of the Reaction Temperature with 10% by Weight of Catalyst According to the Invention $ReO_x/CeO_2$ (i.e. Comprising 10% by Weight of $ReO_x$ with Respect to the Total Weight of Catalyst) [a]

TABLE 4

| Example | Oil bath temperature (° C.) | Reaction temperature (° C.) | Yield (%) (c) | Conversion (%) (b) | Selectivity (%) (b) |
|---|---|---|---|---|---|
| 15 | 165 | 140 | 62 | 88 | 71 |
| 8 | 175 | 145 | 86 | >99 | 86 |
| 16 | 185 | 150 | 81 | >99 | 81 |

[a] reaction conditions: glycerol (92 mg, 1 mmol), 10% by weight of $ReO_x/CeO_2$ (100 mg) and 2-hexanol (3.3 ml), 1300 rpm, 2.5 h, unless otherwise indicated
(b) Selectivity for allyl alcohol and glycerol conversion determined by GC analysis
(c) Yield = Selectivity * Conversion/100.

EXAMPLE 17

Reaction of Glycerol for Obtaining Allyl Alcohol Using 10% by Weight of $ReO_x/CeO_2$ Catalyst According to the Invention with Glycerol with 95% Purity in Water The reaction took place as in the Example 2, but with a glycerol with a 95% purity in water and 2.5 h reaction time. Glycerol (92 mg) and water (5 mg) were mixed beforehand in order to obtain a homogeneous mixture with 2-hexanol. The allyl alcohol yield was 81%, the glycerol conversion was >99%, the allyl alcohol selectivity was 81%.

EXAMPLE 18

Reaction of Glycerol for Obtaining Allyl Alcohol Using 10% by Weight of $ReO_x/CeO_2$ Catalyst According to the Invention with Glycerol of 85% Purity The reaction was carried out as in the Example 2, but with a glycerol with 85% purity and 2.5 h reaction time. Glycerol (92 mg) and water (16 mg) were mixed beforehand in order to obtain a homogeneous mixture with 2-hexanol.

The allyl alcohol yield was 72%, the glycerol conversion was 91%, the allyl alcohol selectivity was 79%.

EXAMPLE 19

Reaction of Glycerol for Obtaining Allyl Alcohol Using 10% by Weight of $ReO_x/CeO_2$ Catalyst According to the Invention with Glycerol of 80% Purity The reaction was carried out as in the Example 2, but with a glycerol with 80% purity and 2.5 h reaction time. Glycerol (92 mg) and water (23 mg) were mixed beforehand in order to obtain a homogeneous mixture with 2-hexanol.

The allyl alcohol yield was 63%, the glycerol conversion was 79%, the allyl alcohol selectivity was 79%.

Results

Glycerol at 95%, 85% and 80% purity in water was studied as starting material for the catalytic reaction in order to determine the effect of water (Table 5). The yield decreased slightly when glycerol with a purity of 95% (Example 17) was used to give the corresponding allyl alcohol with a yield of 81% with a complete conversion (>99%). When glycerol of 85% and 80% purity was used (Examples 18 and 19), yields of 72% and 63% were obtained, respectively. Such effect could be related to the decrease in the boiling point of the liquid mixture when water is added to the glycerol.

Table 5. Reaction of Glycerol with 80 to 99% Purity in Water Using 10% by Weight of $ReO_x/CeO_2$ Catalyst According to the Invention (i.e. Comprising 10% by Weight of $ReO_x$ with Respect to the Total Weight of Catalyst) [a]

TABLE 5

| Example | Glycerol purity in water (%) | Yield (%) (c) | Conversion (%) (b) | Selectivity (%) (b) |
|---|---|---|---|---|
| 8 | >99 | 86 | >99 | 86 |
| 17 | 95 | 81 | >99 | 81 |
| 18 | 85 | 72 | 91 | 79 |
| 19 | 80 | 63 | 79 | 79 |

[a] Reaction conditions: glycerol (92 mg, 1 mmol), water (0, 5, 16, 23 mg for the Examples 8, 17-19 respectively), 10% by weight of $ReO_x/CEO_2$ (100 mg) and 2-hexanol (3.3 ml), oil bath at 175° C., 1300 rpm, 2.5 h, unless otherwise indicated
(b) Selectivity for allyl alcohol and glycerol conversion determined by GC analysis
(c) Yield = Selectivity * Conversion/100.

EXAMPLE 20

Comparison of the Results Obtained Between the $ReO_x/CeO_2$ Catalyst According to the Invention and the Comparative $ReO_3/Al_2O_3$ Catalyst According to EP3124462

Compared with the prior application EP3124462, the catalysts according to the invention have comparable performances in terms of allyl alcohol yield (conversion of glycerol*selectivity toward allyl alcohol). However, when considering the productivity of the catalysts, a much higher productivity can be indicated for the $ReO_x/CeO_2$ catalyst according to the invention, as can be seen in Table 6 below:

TABLE 6

| Parameters | Comparative catalyst $REO_3/Al_2O_3$ according to EP3124462 | Catalyst $ReO_x/CeO_2$ according to the invention |
|---|---|---|
| % by weight of rhenium | 8 | 5 |
| Quantity of catalyst (mg) | 100 | 100 |
| Isoltaed allyl alcohol (mg) | 52.2 | 48.7 |
| Reaction time (h) | 2.5 | 2.5 |
| Productivity (= (g of allyl alcohol/g rhenium)/h | 2.6 | 3.9 |

From the results, it can be seen that a comparable amount of allyl alcohol was produced (48.7 mg versus 52.2 mg), but using a catalyst containing less reactive phase (5% by weight versus 8% by weight), whereby the productivity increased by 50% (3.9 g compared to 2.6 g of allyl alcohol per gram of Re per hour) was obtained.

The ReOx/CeO2 Catalyst According to the Invention Can Thus be Used for Obtaining Allyl Alcohol from Glycerol with a Greatly Increased Productivity.

The invention claimed is:

1. A process for catalyzing the deoxydehydration of glycerol into allyl alcohol, comprising reacting glycerol and a catalyst consisting of rhenium oxide supported by cerium, with the formula $ReO_x/CeO_2$ (I), said process being carried out under heterogeneous conditions in the presence of at least one aliphatic alcohol.

2. The process according to claim 1, wherein said at least one aliphatic alcohol is used as a solvent.

3. The process according to claim 1, wherein said catalyst with the formula (I) is selected from the catalysts in which the amount of $ReO_x$ ranges from 2 to 20% by weight with respect to the total weight of catalyst with the formula (I).

4. A process for producing allyl alcohol from glycerol in the presence of a catalyst, said process comprising only one step of deoxydehydration of glycerol, said process being carried out under heterogeneous conditions, in the presence of i) a catalyst consisting of rhenium oxide supported on cerium oxide, with the formula $ReO_x/CeO_2$ (I) and (ii) at least one aliphatic alcohol.

5. The process according to claim 4, wherein the catalyst with the formula (I) is selected from catalysts in which the amount of $ReO_x$ ranges from 2 to 20% by weight based on the total weight of catalyst with the formula (I).

6. The process according to claim 4, wherein the catalyst with the formula (I) is selected from catalysts in which the amount of $ReO_x$ ranges from 3% to 15% by weight with respect to the total mass of catalyst with the formula (I).

7. The process according to claim 4, wherein the aliphatic alcohol is a monohydric alcohol having from 6 to 10 carbon atoms.

8. The process according to claim 4, wherein the aliphatic alcohol is a monohydric alcohol having from 6 to 8 carbon atoms.

9. The process according to claim 4, wherein the aliphatic alcohol is a monohydric secondary alcohol.

10. The process according to claim 4, wherein the aliphatic alcohol is 2-hexanol or 3-octanol.

11. The process according to claim 4, wherein the deoxydehydration reaction is carried out at a temperature greater than or equal to 140° C.

12. The method according to claim 4, wherein the specific surface area of the cerium oxide used for supporting $ReO_x$ ranges from about 100 m$^2$/g to 300 m$^2$/g as determined by the BET method.

13. The process according to claim 6, wherein the catalyst with the formula (I) is selected from catalysts in which the amount of $ReO_x$ ranges from 4% to 12% by weight with respect to the total mass of catalyst with the formula (I).

14. The method according to claim 4, wherein the specific surface area of the cerium oxide used for supporting $ReO_x$ ranges from 150 m$^2$/g to 250 m$^2$/g as determined by the BET method.

* * * * *